(12) United States Patent  
Nugue et al.

(10) Patent No.: US 7,197,941 B2  
(45) Date of Patent: Apr. 3, 2007

(54) METHOD FOR SELECTING AN INSERT ON THE BASIS OF THE MECHANICAL RESISTANCE THEREOF

(75) Inventors: Jean-Clement Nugue, Courbevoie (FR); Boris Vidal, Luanco (ES); Emmanuel Nourry, Salency (FR)

(73) Assignee: Saint-Gobain Glass France, Courbevoie (FR)

( * ) Notice: Subject to any disclaimer, the term of this patent is extended or adjusted under 35 U.S.C. 154(b) by 423 days.

(21) Appl. No.: 10/473,734

(22) PCT Filed: Mar. 17, 2003

(86) PCT No.: PCT/FR03/00851

§ 371 (c)(1),  
(2), (4) Date: Apr. 13, 2004

(87) PCT Pub. No.: WO03/087785

PCT Pub. Date: Oct. 23, 2003

(65) Prior Publication Data

US 2004/0157071 A1    Aug. 12, 2004

(30) Foreign Application Priority Data

Apr. 15, 2002  (FR) ................................. 02 04776

(51) Int. Cl.  
*G01N 2/24* (2006.01)  
*G01N 3/24* (2006.01)

(52) U.S. Cl. ........................................................ 73/842

(58) Field of Classification Search .................. 73/842  
See application file for complete search history.

(56) References Cited

U.S. PATENT DOCUMENTS 3,087,785 A * 4/1963 Hessinger et al. ....... 423/328.2  
4,998,664 A * 3/1991 Gibson et al. .............. 228/102  
5,589,034 A * 12/1996 Hultman et al. ............ 162/111  
5,847,284 A * 12/1998 Theller ........................ 73/827

FOREIGN PATENT DOCUMENTS

EP    0 387 148     9/1990  
FR    2 697 829     5/1994  
FR    2 808 474    11/2001

* cited by examiner

*Primary Examiner*—Max Noori  
(74) *Attorney, Agent, or Firm*—Oblon, Spivak, McClelland, Maier & Neustadt, P.C.

(57) ABSTRACT

A method for selecting a polymeric insert to be chosen for its mechanical strength qualities to be incorporated into construction of a laminated glazing. The method evaluates the tear strength of the insert, and evaluates adhesion of the insert to at least one glass substrate.

9 Claims, 6 Drawing Sheets

Adhesive strength τ

METHOD FOR SELECTING AN INSERT ON THE BASIS OF THE MECHANICAL RESISTANCE THEREOF

The invention relates to a method of selecting a polymeric insert that has to be chosen for its mechanical strength qualities and is intended, for example, to be used in laminated glazing, preferably giving the glazing acoustic properties.

The term "polymeric insert" is understood to mean a monolithic insert or a composite insert consisting of the assembly of several polymeric elements in the form of layers, resins or films. Preferably, at least one of the elements incorporates polyvinyl butyral (PVB).

Laminated glazing is generally intended for fitting into vehicles or buildings. It has major assets from the standpoint of its mechanical strength. This is because, when an impact occurs, before the glass fractures, the insert advantageously allows some of the energy to be absorbed by viscous dissipation. The role of the insert is also paramount since it guarantees to a great extent the integrity of the structure when the glass is completely shattered, making it possible, thanks to the adhesion of the glass fragments to the film, to prevent glass splinters from being sprayed and consequently preventing injury to people.

Moreover, it is becoming increasingly desirable, for better comfort, for the insert to allow the glazing also to meet acoustic performance criteria so as to attenuate the perception of airborne and/or solid-borne noise reaching the passenger compartment via the glazing.

Polyvinyl butyral (PVB) is widely used for its mechanical properties. It may also provide the laminated glazing with acoustic properties when its composition, including in particular its content of plasticizers, is very suitable.

The insert is selected for providing acoustic properties using a method of determining the critical frequency of the laminated glass and its comparison with the critical frequency of a glass bar. Such a method is described in patent EP-B-0 100 701; an insert is regarded as being suitable when a bar 9 cm in length and 3 cm in width made of a laminated glass, which comprises two glass sheets 4 mm in thickness joined together by said insert 2 mm in thickness, has a critical frequency that differs by at most 35% from that of a glass bar having the same length and the same width and a thickness of 4 mm.

This method of selection, valid for any type of insert intended for being incorporated into laminated glazing, is not only applicable to PVB but also to other polymeric films.

Now, whether used in PVB-laminated glazing or glazing laminated with other polymeric films, in combination or otherwise, so as to obtain "acoustic" glazing, it is paramount for the insert to meet mechanical strength criteria.

This is because building or automobile glazing is required to exhibit excellent response capabilities in terms of impact protection, such as accidental collisions, the falling of an object or a person, vandalism and break-in by throwing objects. Most glazing in use must at least meet the criteria of European Standard EN 356 up to Class P2A.

One method of assessing the tear strength of the insert is known from European patent application EP 1 151 855. For a given thickness of the insert, the value of the critical energy $J_c$ of the insert, which is representative of the energy needed to propagate a crack initiated in the insert, is calculated and if this value is greater than a reference value the insert meets the tear strength criterion.

However, the inventors have demonstrated that some inserts although meeting the tear strength criterion are, nevertheless, not completely satisfactory from the mechanical strength standpoint.

Consequently, the object of the invention is to provide a method of selecting the quality of the mechanical strength of an insert, optionally one that also exhibits acoustic insulation properties, which completes the existing one described in patent application EP 1 151 855 so as to completely guarantee the effectiveness of the insert used for impact protection.

According to the invention, the method, which consists in evaluating the tear strength of the insert, is characterized in that it also consists in evaluating the adhesion of said insert to at least one glass substrate.

According to one feature, the tear strength is evaluated by:
determining the value of the critical energy $J_c$ of the insert, this value being representative of the energy needed to propagate a crack initiated in the insert;
calculating the value of the critical energy normalized to thickness $\tilde{J}_c$ and defined by the equation $\tilde{J}_c = J_c \times e_1$, $e_1$ being the thickness of the insert; and
comparing $\tilde{J}_c$ with a reference value $\tilde{J}_{ref}$ representative of a reference insert formed by a PVB film 0.38 mm in thickness, and equal to 13.3 J/m, the insert meeting the tear strength criterion when $\tilde{J}_c > \tilde{J}_{ref}$.

According to another feature, the adhesion of the insert is evaluated by twisting a specimen of the insert fastened to two glass substrates, by measuring the value of the torsional force or torque for which the separation of the insert from at least one of the substrates is initiated, by calculating the shear strength $\tau$ from this value and by comparing this value with a warning value established for a reference insert formed from PVB.

According to another feature, the mechanical strength of the reference insert with respect to its thickness is mathematically in the form of an approximately parabolic function defined by the critical energy $J_c$ as a function of the adhesive strength $\tau$. The insert whose mechanical strength is to be evaluated meets the tear and adhesive strength criteria when, after evaluating the critical energy and adhesive strength values, these values lie within the parabolic curve that has a minimum corresponding to a value of the critical energy $J_c$ equal to 17,500 J/m².

The insert is selected when, at a temperature of 20° C., its critical energy value is greater than 17,500 J/m² and its shear strength $\tau$ is between 3.8 and 6.9 MPa.

In particular, the insert is selected when, at a temperature of 20° C., its critical energy value is greater than 22,500 J/m² and its shear strength $\tau$ is between 4.8 and 6.1 MPa.

The method according to the invention also consists in selecting the insert for the acoustic properties given to the laminated glazing, the insert meeting the selection of acoustic insulation properties is especially chosen when a bar 9 cm in length and 3 cm in width made of a laminated glass, which comprises two glass sheets 4 mm in thickness joined together by said insert 2 mm in thickness, has a critical frequency which differs by at most 35% from that of a glass bar having the same length and the same width and a thickness of 4 mm.

Preferably, the device which evaluates the shear strength of an insert is characterized according to the invention in that it comprises two jaw systems intended to sandwich a glazing specimen consisting of two glass substrates and the insert, one of the systems being fixed while the other is capable of being moved and rotated, a shaft for rotating the movable-jaw system, a motor for rotating the shaft, a torque meter placed between the motor and the movable-jaw system, and a box that houses the computing elements and includes a display part on which the value of the strength may be read.

The invention also relates to a polymeric insert intended to be incorporated in laminated glazing, characterized in that it has, at a temperature of 20° C., a critical energy value of greater than 17,500 J/m², preferably greater than 22,500 J/m², and a shear strength τ of between 3.8 and 6.9 MPa, preferably between 4.8 and 6.1 MPa.

According to one feature, the insert has a thickness of at least 0.76 mm.

According to another feature, the insert has a thickness e equal to at least $$e_{ref} \times \frac{J_{ref}}{J_c},$$

where:
- $J_c$ is the critical energy value specific to the material of the insert and representative of the energy needed to propagate a crack initiated in the insert;
- $J_{ref}$ is a reference critical energy value corresponding to the critical energy value of a polyvinyl butyral (PVB) film and equal to 35,100 J/m² for a temperature of 20° C. and for a stretch rate on the PVB film of 100 mm/min; and
- $e_{ref}$ is a reference thickness corresponding to that of the PVB film and equal to 0.38 mm.

Advantageously, the insert gives acoustic insulation properties to the laminated glazing for which it is intended. In particular, it is such that a bar 9 cm in length and 3 cm in width, made of a laminated glass comprising two glass sheets 4 mm in thickness joined together by said insert 2 mm in thickness, has a critical frequency which differs by at most 35% from that of a glass bar having the same length and the same width and a thickness of 4 mm.

The insert comprises one or more polymeric elements, preferably at least one PVB film.

Finally, the invention relates to laminated glazing comprising at least two glass sheets and at least one polymeric insert, especially a PVB-based insert, characterized in that the insert has, at a temperature of 20° C., a critical energy value of greater than 17,500 J/m², preferably greater than 22,500 J/m², and a shear strength τ of between 3.8 and 6.9 MPa, preferably between 4.8 and 6.1 MPa.

Advantageously, this glazing is glazing for a vehicle, comprising two glass sheets each having a thickness of between 1.2 and 2.5 mm, and an insert joined to the two glass sheets and having a thickness of at least 0.76 mm.

Preferably, the insert gives this glazing acoustic insulation properties, that is to say, in particular, the insert is such that a bar 9 cm in length and 3 cm in width, made of a laminated glass comprising two glass sheets 4 mm in thickness joined together by said insert 2 mm in thickness, has a critical frequency which differs by at most 35% from that of a glass bar having the same length and the same width and a thickness of 4 mm.

Other advantages and features of the invention will become apparent on reading the description which follows, in conjunction with the appended drawings in which.

The method of the invention is intended for selecting an insert as regards its mechanical strength, the insert being intended to be incorporated into a single or multiple laminated glazing unit, which must withstand hard impacts (EN 356 standard up to Class P2A) or soft impacts (EN 12600 standard). The purpose of the method is to select without having to evaluate mechanical strength by a destructive impact effect.

In the example below, it is desired to know whether an insert is suitable for it to be incorporated into laminated glazing, such as building or automobile glazing.

Figure 1:
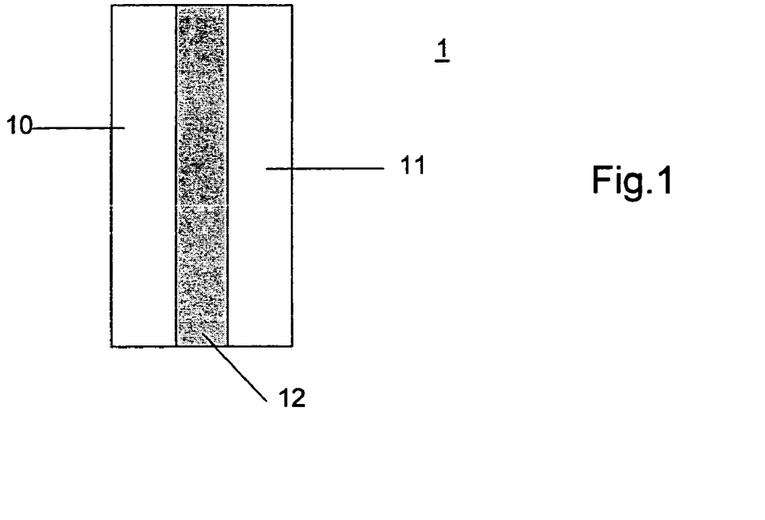
FIG. 1 is a sectional view of single laminated glazing having only one insert film.

The single laminated glazing shown in FIG. 1 comprises two glass substrates 10 and 11 between which is fastened an insert 12.

To select the insert, it is therefore necessary to evaluate its mechanical strength. The inventors have demonstrated that two parameters should be evaluated, namely the tear strength of the insert and the adhesion of the insert to the substrate to which it is joined.

The tear strength is evaluated on the basis of the test and calculation method explained in patent application EP 1 151 855, which we repeat here.

The tear strength of the insert depends on the type of material of which it is made and on its thickness. It is characterized by an energy value representative of the energy needed to propagate a crack initiated in the material. This energy, called the critical energy $J_c$, is different for each type of material and is independent of the thickness of the film, it being expressed in J/m².

The tear strength or critical energy $J_c$ is given in a known manner by an energy method based on the Rice integral J, which defines the energy localized at the root of a crack in a film subjected to very high stresses at the location of a crack. It may be written in the simplified mathematical form (1):

$$J = -\frac{1}{e_1}\left(\frac{\partial U}{\partial a}\right),$$

for a given stretch δ of the specimen tested which will hereafter be called the displacement δ, and in which:
- $e_1$ is the thickness of the specimen;
- a is the length of the crack; and
- U is the potential energy of the specimen.

The above method for calculating the crack root energy J is that developed by Tielking.

Figure 2:
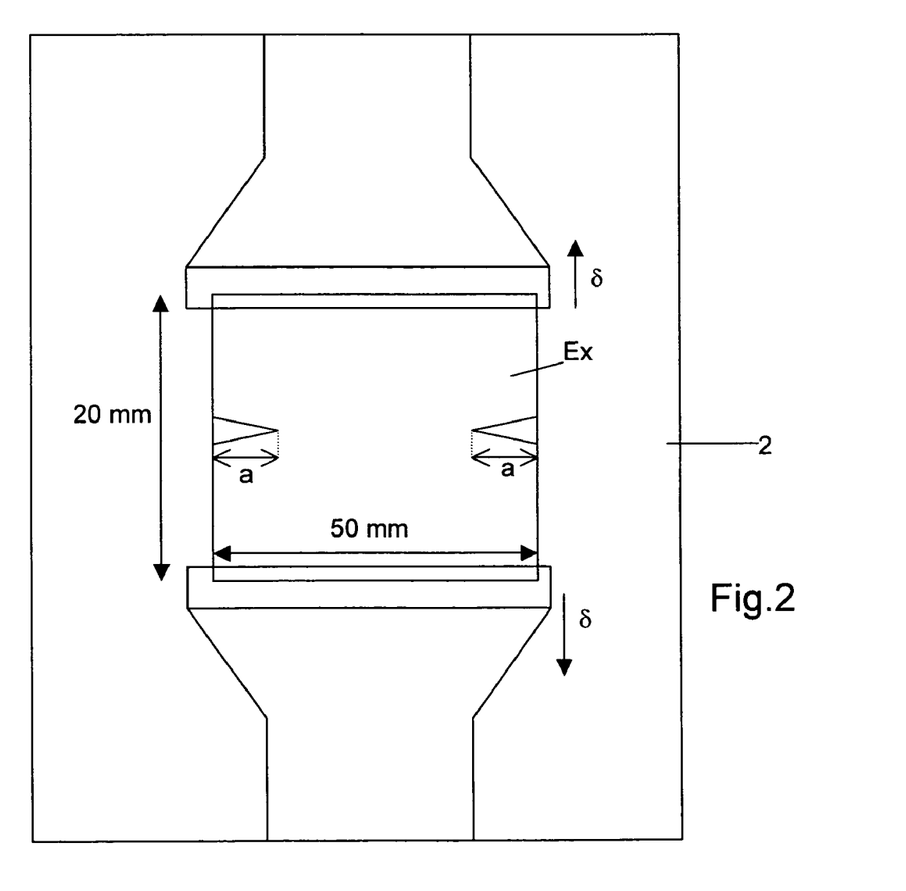
FIG. 2 illustrates diagrammatically an experimental device for evaluating the tear strength of the insert.

The experimental device as illustrated in FIG. 2 is the following:

Tensile tests using a tension-compression machine 2 are carried out on several specimens, for example four specimens $Ex_1$ to $Ex_4$, of the same material and with the same surface area of 100 mm² (50 mm in length by 20 mm in width). Each specimen is notched according to the reference 20 on its sides and perpendicularly to the tensile force, with a different crack length a for each specimen $Ex_1$ to $Ex_4$, corresponding to 5, 8, 12 and 15 mm respectively.

Each specimen Ex is stretched perpendicularly to the cracks 20 at a stretch rate of 100 mm/min over a given stretch length or distance δ and in an environment in which the temperature is 20° C.

This method is used to establish a curve of variation C (FIG. 3) of the crack root energy J as a function of the displacement δ undergone by the specimen and to determine, from this curve, the critical energy $J_c$ for initiating tearing in the specimen.

It is therefore at this critical value $J_c$ that the material tears and that it is consequently mechanically damaged as regards the required mechanical function.

Curve C is obtained from the steps that we explain below. The specimens here are polyvinyl butyral films having a thickness of 0.38 mm.

Figure 4:
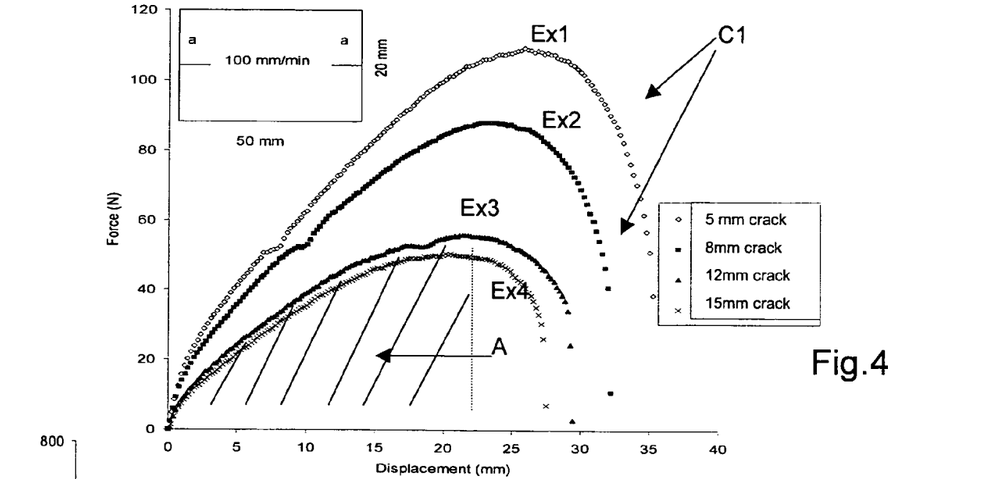
FIG. 4 shows the tensile force exerted on the insert as a function of the stretch of this insert.

Firstly, for each of these specimens $Ex_1$ to $Ex_4$, curve C1 (FIG. 4) representative of the tensile force exerted on the specimen is plotted as a function of the displacement δ undergone by said specimen, which displacement goes from 0 to 40 mm.

From the curves C1 of the specimens, the potential energy U corresponding to a displacement δ given as a function of the increased length a of the crack relative to its initial length is then deduced. The potential energy U is measured by calculating the area A, equivalent to the hatched area shown in FIG. 4, under the curve C1 between 0 mm and the given displacement δ, here 22 mm in the case of the hatched area and corresponding to specimen $Ex_4$.

Figure 5:
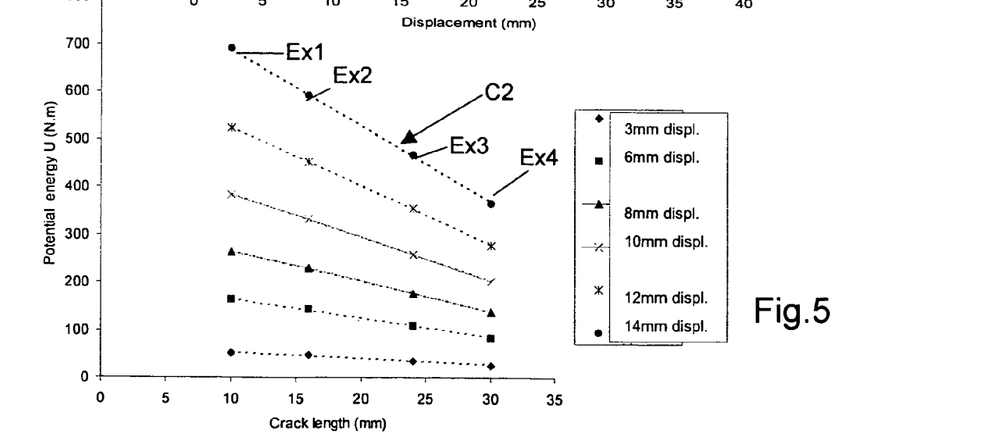
FIG. 5 shows the potential energy of the insert as a function of the stretch of this insert.

Eight displacements δ from 3 mm to 22 mm were considered. It is then possible to plot, for each of the eight displacements, a curve C2 illustrated in FIG. 5, representing the potential energy U as a function of the length a to which the crack has grown.

Curve C2 representative of the potential energy U is a straight line; consequently, the derivative (∂U/∂a), formulated in equation (1), of the energy J is in fact the slope of the line C2 and therefore equal to a constant. The value of J is calculated by dividing this constant by the thickness $e_1$ of the specimen.

After calculating each of the slopes corresponding to the eight displacements, curve C (FIG. 3) representative of the energy J as a function of the displacement δ is established.

Figure 3:
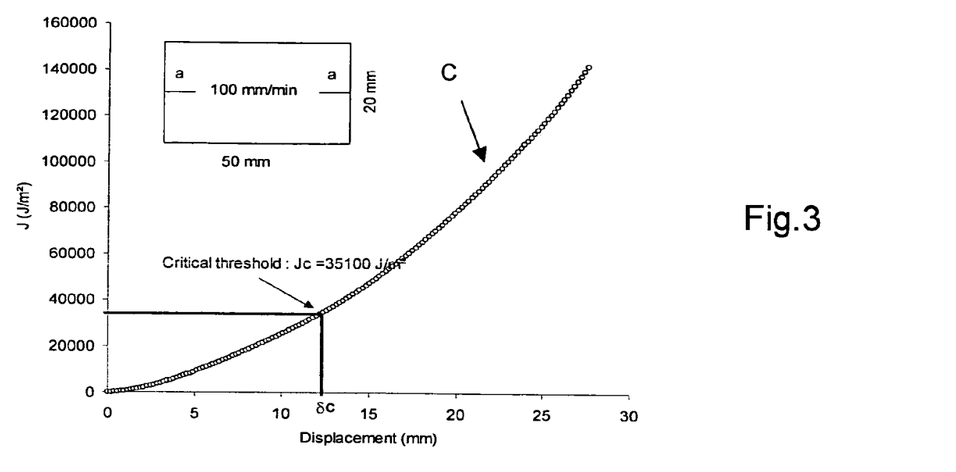
FIG. 3 shows the variation in the energy of the crack root, which crack is produced in the insert.

A video camera, which displays the propagation of the crack 20, is used to detect at which displacement $δ_c$ propagation of the crack in the specimen starts. Using curve C, the corresponding value of the critical energy $J_c$ is deduced from this displacement $δ_c$.

This critical value $J_c$ of 35,100 J/m² in the case of PVB constitutes the reference value $J_{ref}$ of the energy, above which any energy value calculated for another material and according to the method explained above will be considered to be correct so that this material is suitable for meeting the mechanical strength criteria.

Once the specific critical energy value $J_c$ has been calculated, it is, as already explained above, normalized with respect to its thickness, $\tilde{J}_c$ ($J_c \times e_1$) so as to be compared with the reference value of PVB equal to 13.3 J/m and so as to deduce therefrom the suitable thickness e when the thickness $e_1$ is insufficient.

As regards the adhesion of the insert to the substrate to which it is joined, this is evaluated in the following manner.

The adhesion test consists in applying a torsional force to a specimen of the laminated glazing until separation of the insert from at least one of the substrates is initiated.

Figure 6:
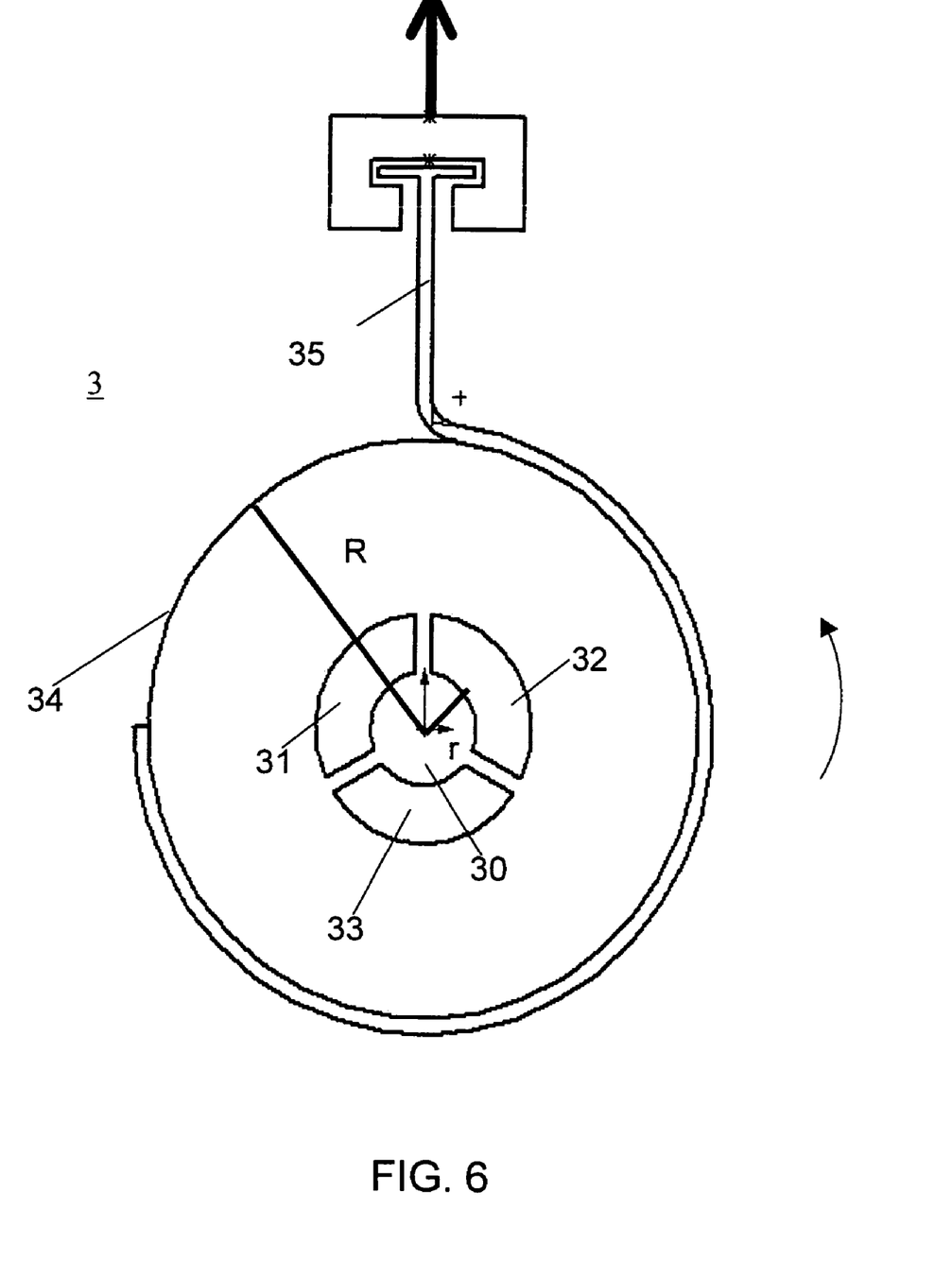
FIG. 6 illustrates a schematic front view of an experimental device for evaluating the adhesion of the insert to the substrate to which it is joined.

The test is carried out on a round specimen 30 of radius r equal to 10 mm by means of a torsion device 3 of known type illustrated in FIG. 6.

The device comprises three jaws 31, 32, 33, a pulley 34 of radius R equal to 100 mm and connected to a drive chain 35 of vertical axis. The jaws are in the form of circular arcs each of 120°, so as to clamp the entire specimen. The surface coating of the jaws is made of a material mechanically compatible with glass, for example aluminum, Teflon® or polyethylene.

One of the jaws is kept fixed against a frame 36 (FIG. 7), while another jaw is fixed to the pulley 34 which is intended to rotate in order to exert torsion on the specimen.

Figure 7:
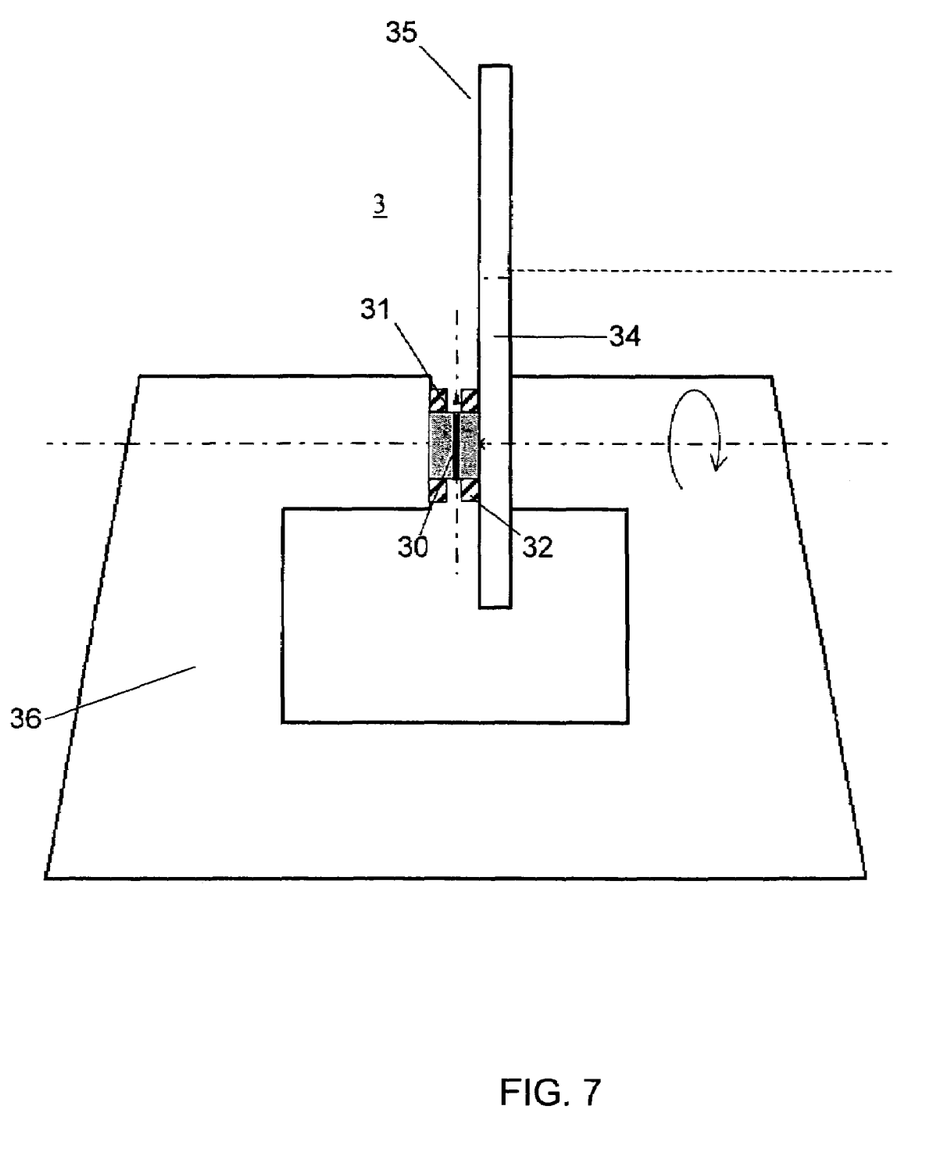
FIG. 7 illustrates a sectional side view of the device shown in FIG. 6.

Rotation of the pulley is caused by the displacement of the chain 34 connected to the pulley. The chain is pulled at a constant speed of at least 35 to 50 mm/min.

The force F needed for the onset of debonding of the insert to appear when the specimen is twisted is measured using a force sensor.

The shear strength may be calculated therefrom by the known formula:

$$\tau = \frac{2FR}{\pi r^3}$$

in which it will be recalled that F is the force needed for the onset of debonding of the insert to occur, R is the radius of the pulley and r is the radius of the specimen.

However, this device is bulky and the tests must therefore be carried out in the laboratory. It is thus ill-suited to measurements of the "process indicator" type on a laminated glazing manufacturing line.

Now, for the manufacture of laminated glazing, although the composition of the polymeric insert is designed to meet the strength values set by the invention, poor adhesion of the insert may nevertheless occur in the finished product because of parameters associated with the process for manufacturing the glazing.

These may, for example, be the conditions under which the insert is stored; if the moisture content is not adequate, the PVB hydroxyl bonds may be altered by water, which will impair the bonding of the insert to the glass. Poor adhesion may also be due to poor washing of the glass and the deposition of ions may result in hydroxyl consumption. The calendering step during assembly of the glass and the insert also acts on the quality of the bonding, the temperature and the compression forces having to be properly controlled.

Thus, the inventors have developed a measurement device other than that described above which is advantageously more compact and easily transportable so as to carry out measurements during monitoring of the manufacture close to the manufacturing line so that it becomes possible to quickly intervene in the process in response to poor measured strength values. This device thus constitutes a management tool for assessing the quality of manufacture of laminated glazing.

Figure 9:
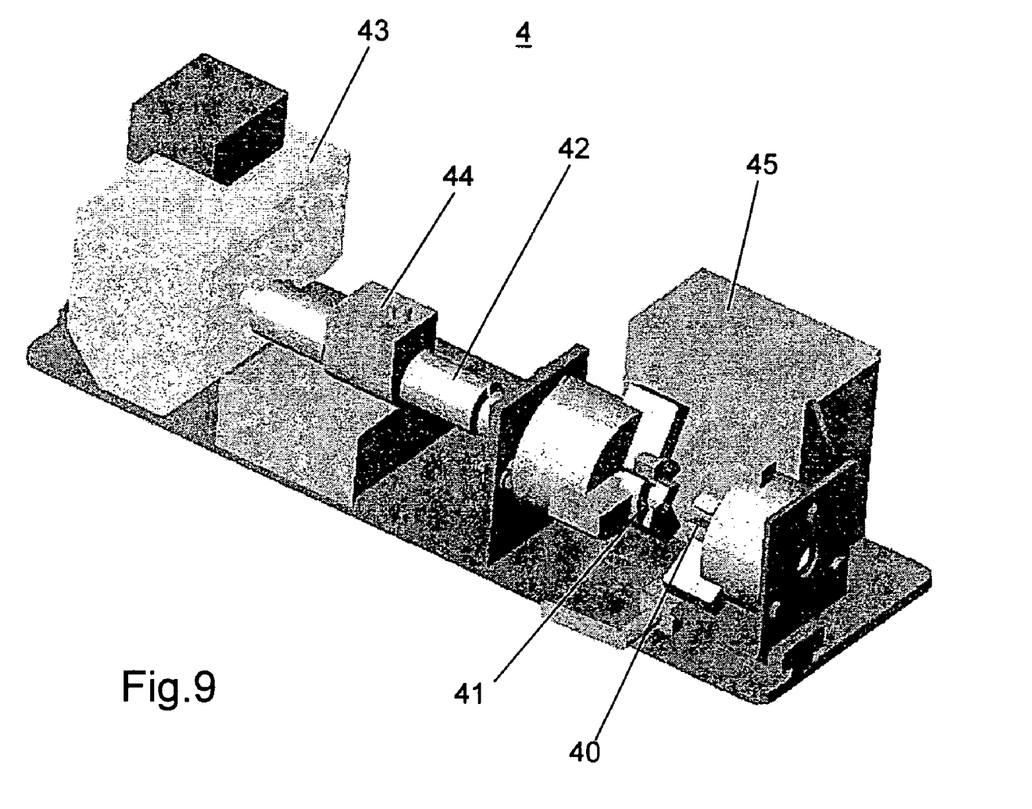
FIG. 9 illustrates a profile view of one embodiment of the device for evaluating the adhesion of the insert to the substrate to which it is joined.

Miniaturized to about 60 cm by 20 cm, the device 4 shown in FIG. 9 comprises two three-jaw systems 40 and 41, a rotation shaft 42, a motor 43 for driving the shaft, a torque meter 44 and a box 45 housing the computing elements.

The round laminated glazing specimen is intended to be sandwiched between the two jaw systems 40 and 41, one of the systems 40 being fixed while the other is capable of being moved and rotated by means of its connection to the shaft 42. The torque meter is placed between the motor and the movable-jaw system 41. The rotation speed of the shaft depends on the thickness of the film. To take an example, for a film 0.76 mm in thickness, the rotation is around 0.08 revolutions per minute.

The system 41 rotates and when the measured torque reverses, the initiation of debonding of the insert has taken place. The torque meter is connected to the computing elements of the box 45, which includes a display part on which the value of the strength τ may be read directly. The adhesion is suitable if this value lies within the range defined by the invention, as explained below.

To have a detailed understanding of the scatter in the value of the strength τ, it is preferred to repeat the test on several specimens, for example, a minimum number of 5 specimens, and to calculate an average of the strength together with its standard deviation.

Finally, the strength value is compared with a warning range within which any value is appropriate for meeting the adhesion criterion. The warning range of the adhesive strength τ is equal to 3.8–6.9 MPa. This warning range was established from a PVB film which, it will be recalled, is considered at the present time as an insert having the highest performance with regard to mechanical strength for meeting the EN356 standard, in particular the characterizing Class P2A of a PVB 0.76 mm in thickness.

To make it easier to compare any insert with the reference insert, which is PVB, the inventors have demonstrated that the mechanical strength may be defined by a reference curve representative of the critical energy $J_c$ as a function of the adhesive strength, this curve having an approximately parabolic shape.

To take an example, FIG. 7 shows this curve for a PVB insert thickness of 0.76 mm. Since the critical energy varies according to the thickness, for a 0.76 mm thickness the reference value of the energy is 17,500 J/m². Since in this graph the energy is not normalized with respect to thickness, it is necessary for any comparison with this curve to test an insert having the same thickness.

Figure 8:
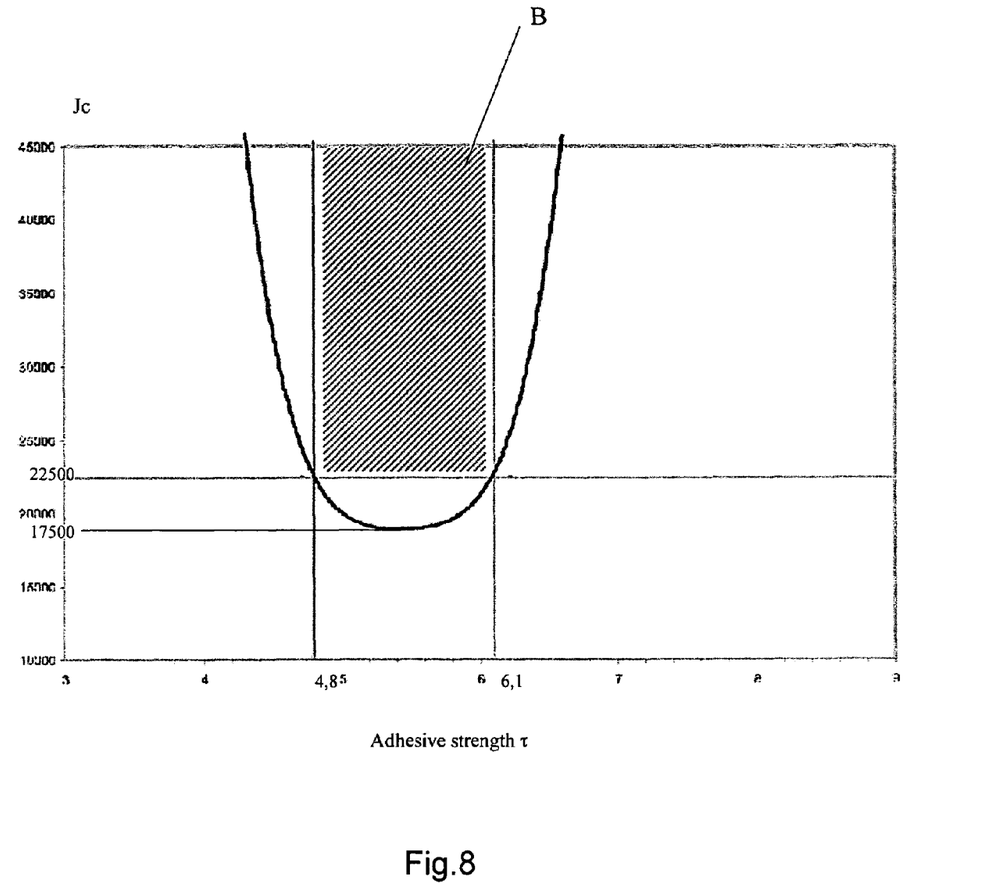
FIG. 8 illustrates the curve of the critical energy as a function of the shear strength for PVB 0.76 mm in thickness.

Consequently, the minimum value that a critical energy must meet corresponds to the minimum of the curve, namely 17,500 J/m², and the adhesive strength must lie within a range centered on the value 5.5 MPa and broadening with the increasing critical energy value. Thus, the critical energy and the adhesive strength values measured on an insert to be tested which lie inside this parabolic curve mean that the insert tested is regarded as being satisfactory from the mechanical strength standpoint.

In order to meet the two criteria—tear strength and adhesive strength—with acceptable reproducibility, the insert must have a critical energy $J_c$ of greater than 17,500 J/m² and an adhesive strength of between 3.8 and 6.9 MPa. Below 3.8 and above 6.9 MPa in the case of the adhesive strength, the laminated glass assembly has too high a probability of poor mechanical behavior. Between 3.8 and 4.8 and between 6.7 and 6.9 MPa, the insert may be regarded as meeting the expected mechanical strength, while not being optimum.

For an optimum insert, a region necessarily lying within the parabola, here the region B, will preferably be considered. In addition, an insert having a minimum thickness of 0.76 mm meeting the Class P2A requirements will be chosen when, preferably, the critical energy $J_c$ is greater than 22,500 J/m² and the adhesive strength τ is between 4.8 and 6.1 MPa.

Other ranges of the adhesive strength τ may be demonstrated for each type of impact, especially on having a relatively low impact energy and with an extensive contact area (soft impact).

If it is desired to select an insert for laminated glazing having both acoustic insulation properties and mechanical strength, the insert will be firstly chosen for its acoustic performance. To achieve this, the reader may refer to the patent EP-B-0 100 701 or patent application EP 0 844 075 which indicate two selection technique variants, these also being summarized in the abovementioned Patent Application EP 1 151 855.

In particular, an insert has acoustic insulation properties when a bar 9 cm in length and 3 cm in width, made of laminated glass comprising two glass sheets 4 mm in thickness joined together by said insert 2 mm in thickness, has a critical frequency which differs by at most 35% from that of a glass bar having the same length and the same width and a thickness of 4 mm.

Once the material has been chosen, its adhesion is evaluated by calculating its shear strength which, if this lies within the desired range, for example 4.8–6.1 MPa for meeting the EN356 standard according to Class P2A, therefore meets the adhesion criterion. Finally, its thickness for meeting the mechanical strength criterion is determined. The thickness e of the insert must at least be equal to $$e_{ref} \times \frac{J_{ref}}{J_c},$$

where:
- $J_c$ is the critical energy value specific to the material of the insert and representative of the energy needed to propagate a crack initiated in the insert;
- $J_{ref}$ is a reference critical energy value which corresponds to the critical energy value of a polyvinyl butyral (PVB) film and equal to 35,100 J/m² for a temperature of 20° C. and for a stretch rate on the PVB film of 100 mm/min; and
- $e_{ref}$ is a reference thickness corresponding to that of the PVB film and equal to 0.38 mm.

The tear strength of the material, which will therefore be identified directly with the critical energy $J_c$, is evaluated only after assessing the acoustic performance of said material and its adhesion. This is because, for the purpose of using an insert for laminated glazing providing acoustic insulation and having to meet the impact protection standards, the approach adopted by the invention is to firstly choose the material suitable for meeting the acoustic insulation criteria and then to test the adhesion performance of this material so as to deduce therefrom the thickness e needed to meet the tear strength criteria.

It should be noted that satisfactory glazing from the mechanical strength standpoint may comprise a monolithic insert of thickness e or a plurality of inserts separated by various substrates, the sum of the thicknesses of the inserts corresponding to the calculated thickness e.

The invention of claimed is:

1. A method for selecting a polymeric insert to be chosen for its mechanical strength qualities to be incorporated into construction of a laminated glazing, the method comprising:

evaluating a tear strength of the insert; and evaluating adhesion of the insert to at least one glass substrate.

2. The method as claimed in claim 1, wherein the evaluating the tear strength includes:

determining a value of critical energy $J_c$ of the insert, this value being representative of energy needed to propagate a crack initiated in the insert;

calculating the value of the critical energy normalized to thickness $\tilde{J}_c$, and defined by the equation $\tilde{J}_c = J_c \times e_1$, $e_1$ being a thickness of the insert; and comparing $\tilde{J}_c$ with a reference value $\tilde{J}_{ref}$ representative of a reference insert formed by a PVB film 0.38 mm in thickness, and equal to 13.3 J/m, the insert meeting tear strength criterion when $\tilde{J}_c > \tilde{J}_{ref}$.

3. The method as claimed in claim 1, wherein evaluating the adhesion of the insert includes twisting a specimen of the insert fastened to two glass substrates, by measuring a value of torsional force or torque for which separation of the insert from at least one of the glass substrates is initiated, by calculating shear strength $\tau$ from this value and by comparing this value with a warning value established for a reference insert formed from PVB.

4. The method as claimed in claim 1, wherein the mechanical strength of the reference insert with respect to its thickness is mathematically in a form of an approximately parabolic function defined by a critical energy $J_c$ as a function of an adhesive strength $\tau$.

5. The method as claimed in claim 4, wherein the insert whose mechanical strength is to be evaluated meets the tear and adhesive strength criteria when, after evaluating the critical energy and adhesive strength values, these values lie within a curve of the parabolic function that has a minimum corresponding to a value of the critical energy of 17,500 J/m².

6. The method as claimed in claim 1, wherein the insert is selected when, at a temperature of 20° C., its critical energy value is greater than 17,500 J/m² and its shear strength $\tau$ is between 3.8 and 6.9 MPa.

7. The method as claimed in claim 6, wherein the insert is selected when, at a temperature of 20° C., its critical energy value is greater than 22,500 J/m² and its shear strength $\tau$ is between 4.8 and 6.1 MPa.

8. The method as claimed in claim 1, further comprising selecting the insert for acoustic insulation properties given to the laminated glazing, the insert meeting selection of acoustic insulation properties is especially chosen when a bar 9 cm in length and 3 cm in width made of a laminated glass, which comprises two glass sheets 4 mm in thickness joined together by the insert 2 mm in thickness, has a critical frequency that differs by at most 35% from that of a glass bar having a same length and same width and a thickness of 4 mm.

9. A device for implementing the method of claim 1, wherein the device evaluates the shear strength of the insert and comprises: two jaw systems configured to sandwich a glazing specimen of two glass substrates and the insert, a first of the two jaw systems being fixed while a second of the two jaw systems is configured to move and rotate; a shaft for rotating the movable-jaw system; a motor for rotating the shaft; a torque meter placed between the motor and the movable-jaw system; and a box that houses computing elements and includes a display part on which a value of the strength may be read.

\* \* \* \* \*